United States Patent [19]

Zimmermann et al.

[11] Patent Number: 5,030,381
[45] Date of Patent: Jul. 9, 1991

[54] PROCESS FOR THE PREPARATION OF STABILIZED ALIPHATIC DIPEROXYDICARBOXYLIC ACIDS

[75] Inventors: Frank Zimmermann, Herten; Thomas Jostmann, Haltern; Hans-Peter Schueller, Marl; Klaus Engel, Recklinghausen, all of Fed. Rep. of Germany

[73] Assignee: Huels Aktiengesellschaft, Marl, Fed. Rep. of Germany

[21] Appl. No.: 360,401

[22] Filed: Jun. 2, 1989

[30] Foreign Application Priority Data

Jul. 6, 1988 [DE] Fed. Rep. of Germany ....... 3822798

[51] Int. Cl.$^5$ ............... C01B 15/10; C07C 407/00; C07C 409/00
[52] U.S. Cl. ............................... 252/186.26; 562/3; 562/4; 562/6
[58] Field of Search ............... 252/186.26; 562/2, 3, 562/6, 4

[56] References Cited

U.S. PATENT DOCUMENTS

| 2,813,896 | 11/1957 | Krimm | 562/6 |
|---|---|---|---|
| 3,192,255 | 6/1965 | Cann | 252/186.26 |
| 3,442,937 | 5/1969 | Sennewald et al. | 252/186.26 |
| 3,494,787 | 2/1970 | Lund | 252/186.26 |
| 4,094,808 | 6/1978 | Stewart et al. | 252/186.26 |
| 4,119,660 | 10/1978 | Hutchins | 562/6 |
| 4,172,086 | 10/1979 | Berkowitz | 562/2 |
| 4,244,884 | 1/1981 | Hutchins et al. | 562/6 |
| 4,287,135 | 9/1981 | Stober et al. | 562/6 |
| 4,314,949 | 2/1982 | Bettle et al. | 562/6 |
| 4,687,592 | 8/1987 | Collins et al. | 252/186.26 |
| 4,707,307 | 10/1987 | Hutton et al. | 562/2 |
| 4,795,594 | 1/1989 | Dankowski et al. | 562/6 |
| 4,801,407 | 1/1989 | Hignett et al. | 252/186.26 |
| 4,818,425 | 4/1989 | Meijer et al. | 252/186.26 |
| 4,828,747 | 5/1989 | Rerek et al. | 252/186.26 |
| 4,874,556 | 10/1989 | Dankowski et al. | 562/3 |

FOREIGN PATENT DOCUMENTS

| 560389 | 2/1959 | Belgium | 252/186.26 |
|---|---|---|---|
| 0000970 | 3/1979 | European Pat. Off. | 562/6 |
| 0074730 | 3/1983 | European Pat. Off. | 252/186.26 |
| 0127783 | 12/1984 | European Pat. Off. | 562/6 |
| 0161485 | 11/1985 | European Pat. Off. | 562/4 |
| 0200163 | 11/1986 | European Pat. Off. | 252/186.26 |
| 2038833 | 2/1971 | Fed. Rep. of Germany | 252/186.26 |
| 2214500 | 10/1972 | Fed. Rep. of Germany | 252/186.26 |
| 2422735 | 12/1974 | Fed. Rep. of Germany | 252/186.26 |
| 2938731 | 4/1980 | Fed. Rep. of Germany | 252/186.26 |
| 3201579 | 6/1982 | Fed. Rep. of Germany | 562/6 |
| 3320497 | 12/1984 | Fed. Rep. of Germany | 562/6 |
| 3628263 | 3/1988 | Fed. Rep. of Germany | 562/6 |

OTHER PUBLICATIONS

Telschig, H., SOFW, "Herstellung Pulverformiger Wasch-und Reinigungsmittel durch den Spruhmisch--Prozeb", Heft 6/1984, 7/1984 and 11/12 1984 (pp. 1-7).
Lund, Jan P.; Nielsen, Donald R., "Encapsulation of Perphthalic Acids with Hydrated Inorganic Salts to Minimize their Tendency to Explode, for Use ... ", Jun. 25, 1969, British #GB 1156240 (Abstract only).
Knapsack, A. G., "Stabilization of Peracetic Acid", Apr. 25, 1966, Neth. Appl. #NL 65/13730 (Abstract Only).
Cann, Allan B., "Stabilization of Carboxylic Peracids", Chemical Abstracts, vol. 58, pp. 4524, 4525, 1963 (British 906,970).
Krimm, Heinrich, "Organic Peracids", Chemical Abstracts, vol. 52, p. 10152 (U.S. 2,813,896).

Primary Examiner—John S. Maples
Assistant Examiner—Joseph D. Anthony
Attorney, Agent, or Firm—Oblon, Spivak, McClelland, Maier & Neustadt

[57] ABSTRACT

Stabilized diperoxydicarboxylic acids are prepared in which diperoxydicarboxylic acids are mixed with sodium sulfate produced in the process to yield improved diperoxydicarboxylic acid granules having good chemical stability despite a high impurity content, safe handling, low bulk density and high abrasion resistance.

41 Claims, 2 Drawing Sheets

PROCESS FOR THE PREPARATION OF STABILIZED ALIPHATIC DIPEROXYDICARBOXYLIC ACIDS

BACKGROUND OF THE INVENTION

1. Field of the Invention

The present invention is directed to stabilized aliphatic diperoxydicarboxylic acids and a process for preparing the same. The stabilized diperoxydicarboxylic acids are useful as bleaching agents.

2. Discussion of the Background

Peroxide compounds are used largely to bleach textiles, because in addition to their good bleaching action they are also cause negligible deterioration of the fabrics.

Sodium perborate has become very important at high washing temperatures since it is a safe and reliable, mild oxidant, and it yields good bleaching results. The drawback with this bleaching agent lies in the non-satisfactory bleaching action at low washing temperatures. The result of the sharp rise in the use of temperature-sensitive synthetic fibers and colored textiles, as well as the trend to conserve energy during the washing process is that, among other things, the significance of a low temperature bleach has increased, thus rendering the search for more active oxidants mandatory.

Peroxycarboxylic acids are suitable low temperature bleaching agents. Their drawback is the high tendency, in their pure form, to decompose exothermally or explode under thermal or mechanical stress so that safe handling without suitable safety measures is not possible.

Processes for safe handling have been developed, such as the preparation of the active bleaching peroxide compound in the washing liquor by reacting safe peroxide compounds (e.g. sodium perborate) with activators. However, these processes suffer from the drawback that there must be high concentrations of the starting peroxide compound and activator in order to compensate the loss of active bleaching species due to the sensitivity of the activators to hydrolysis, the susceptibility of the dosing to variations, and the varying rate at which the components dissolve (See A. Smith et. al., Low Temperature Bleach Systems, AOCS World Conference on Detergents, Montreaux, 1986).

In addition to this, due to the temperature-dependent velocity of the activation reaction, especially at low temperatures, the generation of sufficient concentrations of the active bleaching substance can be delayed, such delays being undesired.

Since these difficulties do not occur when peroxycarboxylic acids are added directly, researchers have tried for a long time to reduce the thermal and mechanical sensitivity of peroxycarboxylic acids by means of stabilization.

Among the available peroxYcarboxYlic acids, interest has focused on the longer chain aliphatic peroxycarboxylic acids, which contain less than 14% activated oxygen. Linear alpha, omega-diperoxydicarboxylic acids have especially preferred properties for general applications, since they have practically no intrinsic odor and good bleaching action even at temperatures ranging from 30° to 40° C. In addition to this, they have surface-active properties. Thus unlike perborate, they do not develop bleaching action everywhere in the washing liquor but rather specifically at the fabric. A systematic study of the bleaching action, published by Lieser et al. (Seifen, Ole, Fette, Wachse, 111, 452 (1985), based on the chain length, shows a maximum at $C=12$, i.e. for the diperoxydodecanedioic acid. Since the raw material dodecanedioic acid that is required to prepare diperoxydodecanedioic acid is also available on a large scale, the diperoxydodecanedioic acid has gained in importance.

To prepare water insoluble alpha, omega-diperoxydicarboxylic acids there exist various processes, whose basic principle, in accordance with DE-AS 10 48 569 is that the corresponding alpha, omega-dicarboxylic acids are converted with hydrogen peroxide using acid catalysts, usually sulfuric acid, in an aqueous medium at temperatures starting at $-50°$ C. The processes of U.S. Pat. Nos. 4,119,660, 4,244,884, 4,314,949, DE-OS 28 61 690, OS 32 01 579, OS 33 20 497 and OS 34 18 450, which also permit in part a continuous reaction, follow this same reaction principle. Usually suspensions containing 2 to 36% solids, whose liquid phase comprises 60 to 80% sulfuric acid in addition to residues of hydrogen peroxide, are obtained as the reaction product.

Further processing of the reaction product is also claimed in U.S. Pat. No. 4,119,660 and DE-OS 28 61 690. The insoluble diperoxydicarboxylic acid is removed by means of filtration, followed by a drying.

These processes suffer from the relevant drawback that during the process highly concentrated diperoxydicarboxylic acids occur that are extremely susceptible to mechanical and thermal strain. Thus these processes do not guarantee safe handling in technical scales.

In contrast, in DE-OS 33 20 496, OS 33 20 497 and OS 34 18 450, the acidic reaction product is neutralized immediately with alkali hydroxides so that there is a mixture of alkali sulfate and diperoxydicarboxylic acid which is separated out. However, the drawback is that due to the temperature and pH peaks in the alkaline region that occur during the neutralization a rapid decomposition of the peroxycarboxylic acids is brought about and thus high loss of the product occurs.

Thus to date there exists no process that permits the further processing of diperoxydicarboxylic acid suspensions, obtained during peroxygenation, in a safe manner without significant loss of the active substance.

Since peroxycarboxylic acids cannot such be safely handled in their pure form, these bleaching agents must be stabilized.

Thus it has been known for a long time that according to BE-PS 560 389, peroxycarboxylic acids can be transmitted to an adequately stabilized, safely manipulable form by mixing with hydratable inorganic salts, in particular sodium sulfate and magnesium sulfate. Numerous methods have been developed to carry out the mixing process. Thus DE-OS 20 38 833 proposes performing the stabilization of aqueous, frozen peroxycarboxylic acid droplets in a fluid bed of magnesium sulfate so that the peroxycarboxylic acid suspension is surrounded by a salt hydrate.

In contrast, the DE-OS 24 22 735 describes processes in which the dry or almost dry peroxycarboxylic acid is blended by mechanical means with the salt chosen as the stabilizator.

Another problem area with peroxycarboxylic acids is their poor chemical stability during storage. The presence of heavy metal ions, which are known as extremely effective decomposition catalysts for peroxides, was postulated as the cause for the poor chemical stability (see R. Criegee in Houben-Weil, Vol. 8, 1952).

To improve the chemical stability, DE-AS 11 74 755, AS 12 80 239 and DE-OS 29 38 731 and OS 22 14 500 propose adding complexing agents as additives for heavy metals such as quinaldine acid, quinoline, polyphosphates, aminophosphoric acids and EDTA. By these measures end products with improved, yet still unsatisfactory chemical stability are obtained.

In order to design the stabilization of peroxycarboxylic acids with sodium sulfate such that the process is economically feasible and in order to largely avoid the disposal problems of sulfuric acid or sodium sulfate solution, it is logical to generate the sodium sulfate required for the stabilization essentially from the process sulfuric acid that is obtained. Therefore, DE-OS 36 28 263 proposes treating the reaction mixtures that are prepared e.g. according to DE-OS 33 20 497 with a purified sodium sulfate that is recovered from a recycled waste liquor and preferably present as a saturated aqueous solution, then neutralizing the mixtures obtained with the sodium hydroxide solution, and finally separating the peroxycarboxylic acid, stabilized with sodium sulfate, from the mother liquor.

Pure sodium sulfate, which is recycled preferably as an aqueous solution into the reaction mixture obtained, is recovered from the mother liquor, which is saturated with sodium sulfate, by means of crystallization. In this process it is absolutely necessary to remove almost all of the impurities in the inhibited peroxycarboxylic acids. To achieve this, primarily the traces of heavy metals, which are especially critical in this method, must be largely discharged by means of the sodium sulfate-containing mother liquor, whereby the heavy metal concentration in the recycled sodium sulfate may be no more than 5 ppm and in the end products in general no more than 2 ppm. This process reduces, of course, the quantity of sodium sulfate-containing waste liquor, yet inhibited peroxycarboxylic acids are obtained that despite an extremely low impurity content, in particular the content of heavy metals, exhibit no improved stability in storage. In addition, on the one hand it is technically expensive to almost completely remove impurities in the ppm range; and on the other hand, a drawback also exists in the risk that with fluctuations in the quality of the added materials or process failures a non-tolerable level of impurities can be very rapidly reached, which in turn leads to drawbacks with respect to the stability in storage and safe handling.

However, in addition to problems concerning safe handling and chemical stability, peroxycarboxylic acid formulations are subject to still other requirements. Since the primary field of application for peroxycarboxylic acids is the bleaching of textiles, peroxycarboxylic acid formulations blended with detergents must have properties that match the conventional components of detergents. To guarantee good flowability and to avoid separation processes in the detergent it is beneficial to use the solid peroxycarboxylic acid formulations at a particle size ranging from 200 to 1250 microns and at bulk densities ranging from 400 to 800 g/l. This specification profile can in principle be attained by agglomeration granulation.

Thus the DE-OS 35 15 712 and the EP-A 256 443 describe processes for granulating in which solid, stabilized peroxycarboxylic acids are agglomerated using a water soluble polymer as the granulating aid. In this process the agglomeration is achieved by spraying an aqueous solution of the granulating aid on the agitated, stabilized peroxycarboxylic acid. According to DE-OS 35 15 712 granulating is also achieved by means of dry blending the granulating aid with the inhibited peroxycarboxylic acid and then spraying with water. A similar process is claimed by the GB-PS 8 127 157 in which polyvinyl alcohol and derivatives are used preferably for granulating in a fluid bed.

By these measures agglomerates can be manufactured according to specification. According to H. Telschig (Seifen, Ole, Fette, Wachse, 1984, 1), however, it is known that the bulk densities of the end products are determined essentially by the bulk density of the starting products. Thus in normal cases a 5 to 10% reduction in the bulk density can be achieved by agglomeration in exceptional cases up to 17%. However, granules with low bulk densities can be manufactured only if initial products with a corresponding low bulk density are available.

Even though a number of problems are solved by means of the described measures, to date there are no sufficiently storage-stable and safe to handle peroxycarboxylic acid formulations, which can be safely prepared and whose specifications correspond to the conventional components of detergents. In addition to this, the use of process sulfuric acid or sodium sulfate that is prepared therefrom for stabilization has not been satisfactorily solved as yet.

A need continues to exist for a safe and unobjectionable process and for improved diperoxydicarboxylic acid granulates, which do not exhibit the drawbacks of the prior art methods and products, and which permits the use of process sodium sulfate.

SUMMARY OF THE INVENTION

One object of the present invention is to provide a safe and reliable process for the preparation of stabilized diperoxydicarboxylic acid granules which are stable to storage and have relatively high decomposition temperatures.

Another object of the invention is to provide a process for preparing diperoxydicarboxylic acid granules which utilizes technical grade starting materials and which is relatively tolerant to heavy metal impurities.

These and other objects which will become apparent from the following specification have been achieved by the present process for preparing an stabilized bleaching agent containing a water-insoluble diperoxydicarboxylic acid, which comprises the steps of:

a) peroxygenating a water-insoluble dicarboxylic acid in the presence of hydrogen peroxide and sulfuric acid, and then separating the resulting product into a diperoxydicarboxylic acid-containing suspension, said suspension containing less than 10% sulfuric acid based on the liquid phase of said suspension, and a substantially peroxide-free filtrate containing a majority of the sulfuric acid, in a multi-stage filtration cascade;

b) neutralizing said filtrate to a pH of 2-6 by adding a sodium hydroxide solution, said solution containing up to 30 ppm heavy metals and up to 50 ppm chloride ions, cooling said neutralized filtrate to crystallize Glauber's salt, recovering said Glauber's salt, and then heating said recovered Glauber's salt to form sodium sulfate;

c) adjusting said suspension to a pH of 2-6 by adding a sodium hydroxide solution, said solution containing up to 30 ppm heavy metals and up to 50 ppm chloride ions, at a temperature below about 40° C.;

d) adding 2-200 wt.%, based on the diperoxydicarboxylic acid content, of a water soluble organic polymer to said adjusted suspension, to obtain a suspension/polymer mixture; and e) mixing said suspension/polymer mixture with said sodium sulfate and drying said mixture to produce said stabilized bleaching agent.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1A:
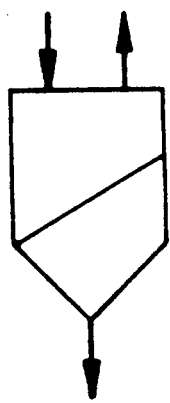
FIG. 1a shows a schematic symbol for a filtration unit.

The problems of the prior art processes are solved by the present invention in that a reaction product that is obtained as a suspension, and containing essentially undissolved diperoxydicarboxylic acid and aqueous sulfuric acid, is separated, while avoiding zones with almost dry diperoxycarboxylic acid, by means of filtration into a filtrate comprising aqueous sulfuric acid and an aqueous suspension of diperoxydicarboxylic acid, containing little sulfuric acid, after which both fractions are neutralized with a sodium hydroxide solution. A purified, water-free sodium sulfate is prepared by means of two-step crystallization from the sodium sulfate solution, which is almost free of diperoxydicarboxylic acid. In the diperoxydicarboxylic acid-containing suspension, water soluble polymers and, if desired, additional additives are dissolved, whereupon the suspension is dehydrated by mixing with the prepared sodium sulfate, thus forming agglomerated granules. These agglomerated granules are characterized by their good chemical stability, safe handling, low bulk densities, and high abrasion resistance. In addition to this, the applied processes make it possible to safely manufacture granules based on the reaction products obtained.

Surprisingly, it has been demonstrated that in the process of the invention there is a distinct tolerance with respect to heavy metals so that good products can be prepared even from reaction mixtures with up to 40 ppm of heavy metals, which occur when technical grade materials are used.

All diperoxydicarboxylic acids that can be prepared through an acid-catalyzed reaction of the corresponding dicarboxylic acids with hydrogen peroxide and that have no appreciable water solubility can be used as organic diperoxydicarboxylic acids. Such diperoxydicarboxylic acids that have no appreciable water solubility are those whose solubility in water at room temperature is less than 1%. Preferred diperoxydicarboxylic acids are alpha, omega-diperoxydicarboxylic acids having 9 to 13 carbon atoms and, in particular, diperoxydodecanedioic acid and diperoxybrassylic acid and mixtures of these.

The reaction product obtained during peroxygenation serves as the starting material for the preparation of stabilized diperoxydicarboxylic acid granules. Normally such peroxygenations are carried out continuously in a multi-step, preferably 3-step agitated vessel cascade in which the water insoluble starting dicarboxylic acid is preferably reacted in the solid form with a mixture of sulfuric acid and hydrogen peroxide. However, economically feasible processes can be realized only by using the more available starting materials on a large scale. At the same time it must be noted that technical grade starting materials contain heavy metals, primarily iron, in the ppm range. Ions of heavy metals such as nickel, chromium, cobalt, zinc, manganese, cadmium, and lead, primarily however, iron and copper, are excellent decomposition catalysts for peroxides.

At the beginning, the liquid phase of the reaction mixture comprises 50 to 70% sulfuric acid, 4 to 20% hydrogen peroxide and 10 to 46% water; the solid phase comprises 1 to 25% dicarboxylic acid, which is preferably metered into the reaction as a powder having an average particle size of less than 100 microns. The reaction is conducted at temperatures ranging from 30° to 50° C. With a residence time ranging from 4 to 14 hours one can thus achieve more than 90% conversion, usually more than 95%. Under these conditions an oxidative degradation of the dicarboxylic acid/diperoxydicarboxylic acid can be largely avoided so that there is almost no loss. The impurities that are dissolved in the reaction mixture from this oxidative degradation of the acids are generally less than 1%.

The reaction yields a suspension whose solid components comprises 1 to 25% of the diperoxydicarboxylic acid produced and residues of non-converted initial dicarboxylic acids; whereas the liquid phase contains 50 to 70% sulfuric acid and can also contain residues of excess hydrogen peroxide, in addition to the organic impurities. The ratio of diperoxydicarboxylic acid produced to unreacted material is at least 90:10, usually at least 95:5.

The reaction product is separated by means of filtration into (1) a filtrate containing the majority of the sulfuric acid and (2) a diperoxydicarboxylic acid suspension in dilute sulfuric acid. In this manner it is possible to prepare crystalline sodium sulfate from the sulfuric acid that is obtained as the filtrate without the presence of diperoxydicarboxylic acid, following neutralization of the acid with a sodium hydroxide solution. The separate further processing of the sulfuric acid is especially advantageous, since in the absence of diperoxydicarboxylic acid, no special safety measures are necessary.

For safety reasons it is preferable that a diperoxydicarboxylic acid suspension with 10 to 40% solid content, preferably 20 to 35%, and whose liquid phase contain less than 10%, preferably less than 5%, sulfuric acid, be generated by means of filtration. For safe implementation it is also generally preferable that during the filtration, zones with almost dry diperoxydicarboxylic acid do not occur. In principle all filtration processes in which there is no significant build-up of filter cakes are suitable for this purpose. Primarily crossflow microfiltration and filtration with agitated filter cartridges of suitable size have been demonstrated to be suitable processes according to the invention. Especially preferred is filtration by means of radial filter cartridges (FIG. 1), whereby adequate stirring of the suspension can also be achieved by means of their rotation and the build up of a filter cake is largely avoided. If the diperoxydicarboxylic acid suspension to be filtered must be pumped, it is necessary to use pumps in which minimum shear forces are developed in order to avoid safety risks.

Figure 2:
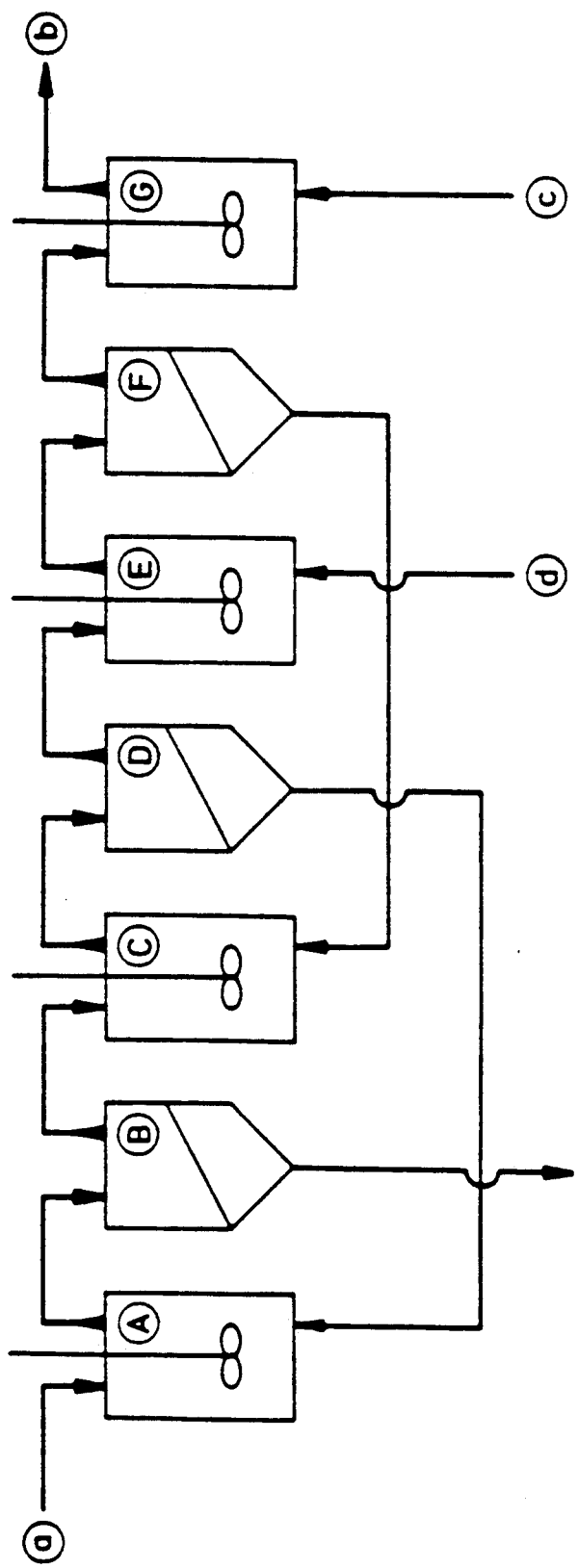
FIG. 2 illustrates a three-step continuous filtration process according to the present invention.

The preferred filtration comprises a multi-step, preferably 2 to 4 steps, in particular a 3-step continuous filtration following the principle of crossflow microfiltration or with agitated filter cartridges, as shown in FIG. 2 for a 3-step filtration. In this figure, "a" is the inflow reaction mixture, "b" is the outflow build-up diperoxydicarboxylic acid suspension, "c" is the inflow additives and neutralization, "d" is the inflow water, "A", "C", and "E" are mixtures, "B", "D", and "F" are filtration units and "G" is neutralization and build-up processes. The reaction product is continuously fed into the agitating vessel A; and 0.1 to 5.5, preferably 0.5 to 2.5, parts of water per part of reaction product are continuously fed into the agitating vessel E. The filtrate that is obtained in the filtration units F and D is recycled preferably completely into the respective preceding filtration step. Thus in FIG. 2 the filtrate from D is re-introduced into the agitating vessel A. By this measure, after having reached a stationary state, 10 to 40 wt.%, preferably 25 to 35 wt.%, sulfuric acid is obtained as the filtrate and a suspension is obtained that contains less than 10 wt.%, preferably less than 5 wt.%, sulfuric acid, based on the liquid portion, and further contains 10 to 40 wt.%, preferably 20 to 35 wt.%, diperoxydicarboxylic acid, based on the total quantity of the suspension.

Preferably the diperoxydicarboxylic acid suspension is then transferred into a following agitating vessel, where it is neutralized to a pH of 2 to 6, preferably 3 to 4, at temperatures below 40° C., preferably below 20° C., through the addition of up to 50 wt.%, preferably 30 to 50 wt.%, aqueous sodium hydroxide solution. At the same time it has been demonstrated that no significant losses of diperoxydicarboxylic acid are associated with the neutralization, if the concentration of sulfuric acid is less than 10 wt.% and the neutralization temperature is below 40° C.

Therefore, the relevant criterion for the filtration is the generation of a diperoxydicarboxylic acid suspension with less than 10 wt.%, preferably less than 5 wt.%, sulfuric acid, based on the liquid portions. In principle, of course, this can also be realized in a one-step procedure; however, then the reaction product must be strongly diluted. The lower the number of steps chosen for filtration, the more water is necessary for dilution, so that the requisite reduction of the sulfuric acid concentration in the suspension is achieved. In order to further process the sulfuric acid obtained as the filtrate, the sulfuric acid concentration in the filtrate should range from 10 to 40 wt.%, preferably from 25 to 35 wt.%. In order to attain this, a 2 to 4 step filtration is preferred, in particular a 3-step filtration. The diperoxydicarboxylic acid content, to be adjusted in the respective filtration steps, should range from 10 to 40 wt.%, preferably from 25 to 30 wt.%, whereby the solid content can be adjusted to the same or different level in all steps. Solid contents lower than 10 wt.% are unsuitable with respect to further processing. When solid contents are higher than 40 wt.%, the suspension can usually be no longer sufficiently agitated or pumped.

Neutralization of the sulfuric acid remaining in the diperoxydicarboxylic acid suspension is conducted with a sodium hydroxide solution. Due to the direct further processing of this suspension, the sodium hydroxide solution that is used must meet certain purity criteria. Thus the chloride ion content should be less than about 50 ppm. The heavy metal concentration is not critical and can amount up to about 30 ppm.

The diperoxydicarboxylic acid suspensions can be either immediately further processed or preferably treated with additives. The object of the added additives is to improve the chemical stability of the diperoxydicarboxylic acid or the mechanical stability of the granulated final products. According to the invention, especially preferred is the addition of 0 to 20 wt.%, preferably 2 to 20 wt.% based on the diperoxydicarboxylic acid content, of a phosphate, preferably sodium tripolyphosphate, 0 to 150 wt.%, preferably 20 to 100 wt.% magnesium sulfate heptahydrate, 0 to 10 wt.%, preferably 0 to 3 wt.% of a complexing agent for heavy metals, 0 to 20 wt.%, preferably 0 to 5 wt.% of a silicate, preferably sodium metasilicate and 2 to 200 wt.%, preferably 5 to 50 wt.% of a water soluble organic polymer. In particular, polymeric carboxylic acids, preferably homopolymers of unsaturated carboxylic acids such as acrylic acid, maleic acid and crotonic acid, as well as the copolymers thereof and with ethylene, propylene, butene, vinyl acetate and styrene are suitable as water soluble polymers.

In addition to the addition of magnesium sulfate heptahydrate, it is also possible to generate magnesium sulfate in situ by neutralizing the remaining sulfuric acid in the diperoxydicarboxylic acid suspension after filtration, in whole or in part with magnesium oxide or magnesium hydroxide. If necessary, the conventional complexing agents may be added, preferably quinaldinic acid, quinoline, aminophosphoric acids, and ethylenediamine tetraacetic acid which are suitable for complexing heavy metals.

Even with the addition of the additives contamination with chloride ions is possible so that one must take care that, following the addition of the additives, the chloride concentration remains below 50 ppm. The heavy metal content is not critical and can amount up to 30 ppm following the addition of the additives.

Following filtration, 10 to 40 wt.%, preferably 25 to 35 wt.% sulfuric acid which may contain residues of excess hydrogen peroxide is obtained as the filtrate.

It has been demonstrated that following the essentially complete separation, according to the invention, of the diperoxydicarboxylic acid and sulfuric acid, it suffices to recycle the sulfuric acid into sodium sulfate in the conventional manner by means of neutralization and crystallization. This simple further processing is facilitated by the surprisingly high tolerance of the process of the invention to traces heavy metals in the sodium sulfate.

The sulfuric acid thus obtained is neutralized to a pH of 2 to 6 with a sodium hydroxide solution (up to 50 wt.%) which contains less than 50 ppm chloride ions, and less than 30 ppm heavy metals at temperatures ranging from 30° to 60° C., preferably from 35° to 45° C., and thereafter cooled. The Glauber's salt thus obtained is removed by means of centrifuging or filtering. At temperatures ranging from 60° to 110° C. and pressures ranging from 10 to 220 mbar, the evaporative crystallization of the Glauber's salt is conducted by heating the Glauber's salt until a solid content ranging from 15 to 50 wt.% is attained, whereupon the sodium sulfate is removed by filtering or centrifuging and dried, e.g., in a convection or contraction dryer until the residual moisture is below 0.5 wt.%. In this manner sodium sulfate is obtained with a bulk density ranging from 1000 to 1500 g/l and a particle size distribution with at least 90% of the particles below 200 microns, preferably below 100 microns. Following this crystallization, the chloride content is generally below 50 ppm.

When further processed according to the process of the invention, the heavy metal content can be up to 30 ppm without any significant negative impact on the stability of the end product.

The granulated end product is manufactured by mixing the crystalline sodium sulfate prepared during the process as described above with the diperoxydicarboxylic acid suspension. In the mixing process the suspension containing the diperoxydicarboxylic acid is dehydrated whereby the water that is introduced with the suspension is bonded with the sodium sulfate as waters of hydration. Despite the high heavy metal content, the result of using the process sodium sulfate is a drastic increase in the chemical stability and decrease in the tendency to decompose.

However, according to the invention it is especially advantageous to use diperoxydicarboxylic acid suspensions, while adding stabilized additives, which are then enriched in the end product in the spacial vicinity relative to the diperoxydicarboxylic acid, whereby only a relatively low concentration of additives is necessary. Water soluble polymers are especially important for the further improvement of the chemical and mechanical stability of the granules.

The dehydration caused by mixing the suspension with the sodium sulfate results in a coating of the diperoxydicarboxylic acid with the polymer. The effective shielding connected with this process of the diperoxydicarboxylic acid against decomposition-promoting components is reflected in the distinct improvement of the chemical stability, which at the same time improves the tolerance with respect to traces of heavy metals in the sodium sulfate.

In addition to this, a very effective adhesion of individual components is achieved by means of the dissolved polymer, thus forming agglomerated granules, so that the result is surprisingly mechanically stable end product having a instant character. Furthermore, due to the excellent adhesive properties of the polymers used, a drastic reduction in the bulk density is attained. In the present process, purified sodium sulfate is produced in the process and used to make the final product. Following crystallization and drying, the sodium sulfate precipitates as heavy sulfate having a bulk density ranging from 1000 to 1500 g/l and a particle size distribution of at least 90% below 200 microns, preferable below 100 microns. When this sodium sulfate is used, following mixing with the suspension obtained with the dissolved polymer, a agglomerated granule is obtained, which following mild drying, has bulk densities ranging from 400 to 800 g/l, preferably 500 to 650 g/l, and particle sizes of at least 90% in the range of 200 to 1250 microns. The excellent mechanical stability of the agglomerated granules can be seen when measuring the abrasion resistance on an Engelsman tumble screen with screen apertures of 200 microns. Two hours of mechanical stress yields less than 6% dust in the form of particles having particle sizes below 200 microns.

If other additives are added to the suspension in addition to the water soluble polymers, the chemical stability can be further improved. In particular, when water soluble polymers are combined with magnesium sulfate and phosphates, preferably sodium tripolyphosphate, a synergistic improvement in the chemical stability occurs that cannot be achieved when a single additive is used alone. In addition, the object is to significantly increase the decomposition temperature of the dry granular materials.

The mixing process can be conducted in commercially available agglomerators operating on the spray-mix principle. In order to achieve a homogeneous distribution of the diperoxydicarboxylic acid in the granular material, the diperoxydicarboxylic acid suspension is applied, preferably finely dispersed, by means of a nozzle or spray roller on the agitated sodium sulfate.

According to the invention, especially suitable devices are agglomerators with rotating drums or cones, continuous working vertical agglomerators, and continuous "zig-zag" agglomerators such as fluid-bed granulators. Such agglomerators are preferred that facilitate a continuous process, in particular the fluid-bed granulators. The continuous agglomeration in the fluid bed is conducted in multiple steps, preferably in a 2 to 5 step granulator at dwell times ranging from 20 to 60 min and at inlet air temperatures ranging from 60° to 100° C., preferably from 65° to 85° C.

The inlet air temperature can be precision adjusted in such a manner that the temperature in the fluid bed during granulation ranges from 25° to 60° C., preferably from 30° to 40° C. It is especially advantageous to remove the water during the granulating process in the fluid bed. Thus granules with up to 43% diperoxydicarboxylic acid can be prepared without their adhering or sticking to one another.

Depending on the process variation, the water content of the moist granules obtained can amount up to 35 wt.%. To largely remove the moisture, continuous drying in the fluid-bed is especially preferred. Multistep, preferably 2 to 5 step, and in particular 3-step, fluid bed dryers may be used. The inlet air temperature ranges at first from 90° to 140° C. and is then reduced down to 50° to 90° C., corresponding to the number of steps chosen. The inlet air temperature is set according to the temperature in the fluid bed, which may be at most 60° C., preferably at most 55° C. for safe implementation. The dwell times range from 10 to 60 min, whereby granules with residual moisture of less than 10 wt.%, preferably less than 5%, are obtained.

By means of these measures a bleaching agent, which is inhibited with process produced sodium sulfate, is obtained. The bleaching agent is characterized by a content of less than 50 ppm chloride ions and a tolerable content of up to 30 ppm heavy metals. In addition to this, based on the diperoxydicarboxylic acid, it may also contain 2 to 200 wt.%, preferably 5 to 50 wt.%, of a water soluble organic polymer, 0 to 120 wt.%, preferably 2 to 20 wt.%, of a phosphate, preferably sodium polyphosphate, 0 to 150 wt.%, preferably 20 to 100 wt.%, magnesium sulfate, 0 to 10 wt.%, preferably 0 to 3 wt.%, of a complexing agent for heavy metals and 0 to 20 wt.%, preferably 0 to 5 wt.% of a silicate as additional stabilizing additives. These components are not homogeneously distributed over the granules by means of the process of the invention but rather are enriched in the vicinity of the diperoxydicarboxylic acid. The described measures cause a distinct synergistic effect so that the bleaching agent is characterized by its remarkable chemical stability and low tendency to decompose in heat.

The preferred field of application for this bleaching is the bleaching of the textiles and fibers. At the same time the bleaching agent can be used alone or in combination with detergents. Especially advantageous is the blending with detergents, especially since with respect to the particle size distribution, bulk density and mechanical stability, the bleaching agent corresponds largely to the specification required for components of detergents; and in addition to this, it has excellent chemical stability.

Other features of the invention will become apparent during the course of the following descriptions of exemplary embodiments which are given for illustration of the invention and are not intended to be limiting thereof.

EXAMPLES

The stability in storage and tendency of diperoxydicarboxylic acids to decompose are negatively effected by chloride ions.

The starting materials added in the examples contained the following listed concentrations of chloride ions:

| Starting material | chloride ions (ppm) |
|---|---|
| 96% sulfuric acid | <1 |
| 40% hydrogen peroxide | <5 |
| dodecanedioic acid | <1 |
| brassylic acid | <2 |
| 50% sodium hydroxide solution | 20 |
| 30% sodium hydroxide solution | 12 |
| magnesium sulfate heptahydrate | 45 |
| sodium tripolyphosphate | 160 |
| polyacrylic acid | <3 |
| ethylene-maleic acid copolymer | <5 |

The following examples explain the process of the invention.

EXAMPLE 1

Preparation of a Reaction Mixture with Diperoxydode-canedioic Acid (DPDDA)

A mixture comprising 5750 g of 96% sulfuric acid and 2350 g of 40% hydrogen peroxide was introduced into a stirred vessel and treated with 1060 g of powdered dodecanedioic acid (DDA) at 45° C. over 30 minutes. After 4 hours of reaction time, a mixture of the following composition was obtained:
11.5% solid (97.4% DPDDA+2.6% DDA)
88.5% liquid (67.2% $H_2SO_4$, 4.1% $H_2O_2$, 27.3% $H_2O$)

EXAMPLE 2

Continuous Filtration of the Reaction Mixture

Figure 1B:
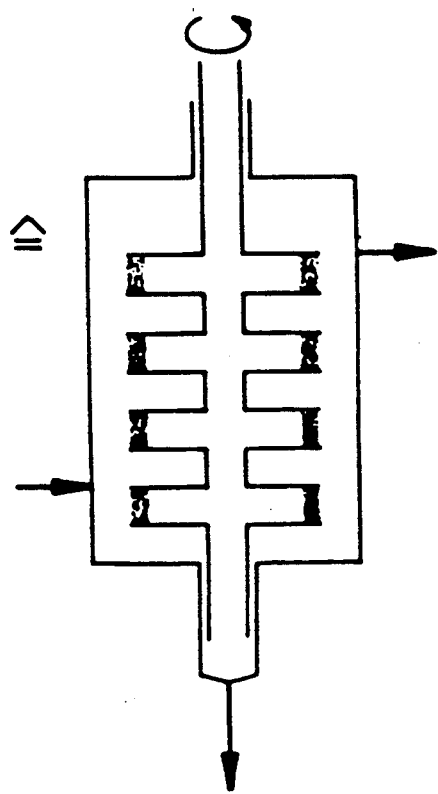
FIG. 1b shows a preferred filtration unit by means of radial filter cartridges.

In a filtration cascade corresponding to FIG. 1, 5 kg/h of a reaction mixture, comprising 52.0% $H_2SO_4$, 19.4% DPDDA, 0.3% DDA, 1.3% $H_2O_2$, 0.29% of water soluble organic components and 26.0% $H_2O$ (19.7% solids, 98.5% DPDDA, 1.5% DDA composition) was continuously fed into the mixing vessel A and 6 kg $H_2O$ was fed into mixing vessel E. The pump performance was set to approximately 7 to 7.5 l/h so that in every filtration step, the mixture was thickened to a solid content of approximately 25%. The filtrate of the filtration units F or D was completely recycled into the mixing vessel C or A. Upon reaching the stationary state, a 35.1% $H_2SO_4$ (7 kg/h) leaves as filtrate from filtration step B, and 4 kg/h of a suspension containing 25.2% solids and a residual $H_2SO_4$ content of 4.9% (based on the liquid portions) from filtration step F. In the following agitating vessel G the suspension was neutralized continuously to pH 3.5 by adding 3.5 g/h of 50% NaOH so that a suspension of the following composition was obtained.
22.9% DPDDA
0.5% DDA
5.3% $Na_2SO_4$
71.1% $H_2O$
Water insoluble solid content: 97.9% DPDDA+2.1% DDA Filtrate: 35.1% $H_2SO_4$.

EXAMPLE 3

Neutralization of Filtrate and Crystallization

In a stirred vessel, 200 kg of 35.1% $H_2SO_4$ that was obtained as filtrate according to Example 2 was neutralized over 4 hours to pH 3.5 at 40° C. by adding 115 kg of a 50 wt.% sodium hydroxide solution. The temperature was lowered over 8 hours to approximately 3° C., centrifuged and thus 214 kg of a moist Glauber's salt was obtained. The Glauber's salt was melted at 50° C. and the melt produced was decanted from the sediments.

At 80° C., evaporative crystallization was conducted with the melt under vacuum until a solid content of approximately 47% was attained. Following centrifuging and drying, 62 kg $Na_2SO_4$ with a residual moisture content of 0.8%, a bulk density of 1230 g/l and a particle size distribution of 90% below 100 microns was obtained. The heavy metal content was 20 ppm and the chloride content was 5 ppm.

The drawbacks of direct neutralization of the reaction product are clarified with the aid of Examples 4 and 5 (reference examples).

EXAMPLE 4

In situ Stabilization of DPDDA by Directly Neutralizing the Reaction Mixture 4500 g of the reaction mixture that was obtained according to Example 1 was diluted with 5250 g of water and neutralized to pH 3.5 over 3 hours at 40° C. with 30 wt.% NaOH. Following cooling to 20° C., the mixture was centrifuged and dried at 45° C. 1650 g DPDDA stabilized with $Na_2SO_4$ was obtained.
Composition:
25.9% DPDDA
2.6% DDA
67.4% $Na_2SO_4$
3.7% $H_2O$
Balance of the water soluble components
Composition prior to neutralization: 97.4% DPDDA, 2.6% DDA
Composition following neutralization: 90.0% DPDDA, 9.1% DDA
Tables 1, 2 and 3 present further analysis data.

EXAMPLE 5

4500 g of the reaction mixture that was obtained according to Example 1 was treated with 5250 g of a 30 wt.% $Na_2SO_4$ solution and neutralized to pH 3.5 over 3 hours at 40° C. with 30 wt.% NaOH. Following cooling to 20° C., the mixture was centrifuged and dried at 45° C. 3182 g of DPDDA stabilized with $Na_2SO_4$ was obtained.
Composition:
13.1% DPDDA
2.2% DDA
80.2% $Na_2SO_4$
4.2% $H_2O$ Balance of the water soluble components
Composition prior to neutralization: 97.4% DPDDA, 2.6% DDA
Composition following neutralization: 85.6% DPDDA, 14.4% DDA
Tables 1, 2 and 3 present more analysis data.

EXAMPLE 6

Agglomeration Granulation with Diperoxydodecanedioic Acid

A 15 liter Patterson Kelly V mixer was loaded with 6 kg of the sodium sulfate that was obtained according to Example 3. At 50 rpm, 1800 g of a DPDDA suspension adjusted to pH 4 and comprising 32.0% DPDDA, 0.3% DDA, 3.9% $Na_2SO_4$, 4.8% ethylene maleic acid copolymer (molecular weight approximately $10^4$), 3.2% $Na_5P_3O_{10}$ and 56.1% $H_2O$, was sprayed into the mixer over 3 minutes. The product was granulated for 3 minutes more at 30 rpm and dried 20 minutes in a fluid bed. The inlet airflow was 80 $m^3$/h. At the start of drying, the temperature of the inlet air was 120° C., and was lowered in the course of drying approximately 70° C. so that the fluid bed exhibited temperatures ranging from 35° to 40° C.

Composition of the granules:
8.5% DPDDA
0.1% DDA
1.3% ethylene maleic acid copolymer
0.8% $Na_5P_3O_{10}$
86.0% $Na_2SO_4$
3.2 $H_2O$ Balance of the water insoluble components
Ratio of DPDDA to DDA prior to granulation: 99.1%:0.9%
Ratio of DPDDA to DDA following granulation: 98.8%:1.2%
Tables 1, 2 and 3 contain more analysis data.

EXAMPLE 7

Agglomeration Granulation with Diperoxydodecanedioic Acid

In a fluid bed containing 5 kg of the $Na_2SO_4$ prepared according to Example 3, 5 kg of a DPDDA suspension, as obtained according to Example 2 (22.9% DPDDA, 0.5% DDA, 5.3% $Na_2SO_4$ 7.1% $H_2O$) was sprayed into the mixer over 20 minutes. At the start of pelletizing the inlet airflow was increased to approximately 75° C., so that the temperature in the fluid bed ranged from 30° to 35° C. Following granulation, the mixture was dried for 20 minutes at an inlet airflow of approximately 80 $m^3$/h and an inlet air temperature of approximately 80° C., whereby the temperature of the fluid bed increased to approximately 50° C.

Composition of the granules:
18.2% DPDDA
0.4% DDA
79.0% $Na_2SO_4$
2.4 $H_2O$

Balance of the water insoluble components
Ratio of DPDDA to DDA prior to granulation: 97.9%:2.1%
Ratio of DPDDA to DDA following granulation: 97.8%:2.2%
Tables 1, 2 and 3 contain more analysis data.

EXAMPLES 8 to 10

Examples of Granules with Diperoxydodecanedioic Acid

Analogous to Example 7, various DPDDA and $Na_2SO_4$ granules were prepared in the fluid bed whose difference, on the one hand, lay in the quality of the $Na_2SO_4$ added and, on the other hand, in the addition of the additives (such as $MgSO_4$, $Na_5P_3O_{10}$, water soluble polymers) to the DPDDA suspension prior to conducting the granulation. Of course, these measures do not lead to any significant change in the granulating and drying process, yet a significant influence can be seen on the granule properties, which are explained in Tables 1, 2 and 3.

Example 11

Agglomeration Granulation with Diperoxybrassylic Acid

The testing procedure corresponds to the procedure outlined in Example 7. 5 kg $Na_2SO_4$ was used, into which was sprayed 6 kg of a diperoxybrassylic acid suspension, comprising 21.4 wt.% diperoxybrassylic acid, 0.8% brassylic acid, 5.2% $Na_2SO_4$, 3.2% polyacrylic acid ($10^5$ molecular weight), 1.0% $Na_5P_3O_{10}$, 5.1% $MgSO_4$ and 63.3% $H_2O$ over 20 minutes. The composition of the granules and other analysis data are shown in Tables 1, 2 and 3.

TABLE 1

| Example | Composition of Peracid Granular Material in Percent by Weight | | | | | | | |
|---|---|---|---|---|---|---|---|---|
| | 4 | 5 | 6 | 7 | 8 | 9 | 10 | 11 |
| peracid (potentiometrically) | 25.9 | 13.1 | 8.5 | 18.2 | 18.4 | 17.8 | 23.1 | 17.9 |
| carboxylic acid | 2.6 | 2.2 | 0.1 | 0.4 | 0.4 | 0.4 | 0.5 | 0.7 |
| $Na_2SO_4$ | 67.4 | 80.2 | 86.0 | 79.0 | 75.9 | 74.2 | 62.3 | 70.1 |
| $MgSO_4$ | — | — | — | — | — | 4.3 | 5.6 | 4.3 |
| $Na_5P_3O_{10}$ | — | — | 0.8 | — | — | 0.8 | 1.1 | 0.8 |
| polyacrylic acid | — | — | 1.3 | — | 2.7 | — | 3.5 | — |
| ethylene-maleic acid copolymer | — | — | — | — | — | 2.7 | — | 2.7 |
| $H_2O$ | 3.7 | 4.2 | 3.2 | 2.4 | 2.6 | 3.8 | 3.9 | 3.4 |
| heavy metal (ppm) | 23 | 24 | 20 | 20 | 21 | 20 | 20 | 19 |
| chloride (ppm) | <5 | <5 | <1 | <1 | <1 | <1 | <1 | <1 |
| 0.2-1.0 mm (%) fraction | 87.5 | 89.1 | 94.2 | 62.8 | 90.5 | 96.4 | 97.0 | 91.2 |
| bulk density (g/l) of the fraction | 990 | 1030 | 575 | 915 | 535 | 495 | 580 | 615 |
| dust <200 mm after 2 h (%) | — | — | 2.9 | 65.0 | 2.1 | 1.4 | 1.9 | 5.2 |

Stability in Storage of the Peracid Granules

To determine the storage stability, 200 g of peracid granules were stored at 30° or 50° C. respectively. At the beginning and after 10, 30, and 60 days of storage, the peracid content was determined potentiometrically by means of titration with NaOH. The granules were stirred in isopropanol and water (80:20) in the presence of magnesium sulfate and filtered. In the filtrate the peracid content was determined potentiometrically. The test results show that the use of process produced $Na_2SO_4$ results in a distinct improvement in the storage stability. When the peracid is also shielded by means of inert water soluble polymers and/or additions of $MgSO_4$ and/or $Na_5P_3O_{10}$, granules are obtained that are characterized by their excellent storage stability at higher temperatures.

TABLE 2

Storage stability at 50° C. (peracid content in % based on initial content)

| storage period (days) | Example |||||||||
|---|---|---|---|---|---|---|---|---|---|
| | 4 | 5 | 6 | 7 | 8 | 9 | 10 | 11 | 12 |
| 10 | 4.0 | 3.9 | 87 | 71 | 5.8 | 88 | 90.0 | 91.5 | 88.5 |
| 30 | — | — | 77 | 43 | | 78 | 82 | 85 | 81 |
| 60 | — | — | 69 | — | | 67 | 76 | 79 | 70 |

Storage stability at 30° C.

| storage period (days) | Example ||||||
|---|---|---|---|---|---|---|
| | 6 | 7 | 9 | 10 | 11 | 12 |
| 10 | 99 | 94 | 97 | 98 | 99 | 96 |
| 30 | 95.5 | 85 | 92 | 96 | 98.5 | 94 |
| 60 | 94 | 76 | 87 | 92 | 95.5 | 91.5 |

DETERMINATION OF DECOMPOSITION TEMPERATURE

For determination of decomposition temperatures, the granules were dried for 24 hours under vacuum at room temperature. 10 g of granular material was filled into an aluminum block ad heated at 2.5° C./minute. The temperature at which the sample decomposed under exothermic reaction was measured. The tests showed that by using process produced $Na_2SO_4$ according to the process of the invention, a definite increase in the decomposition temperature can be achieved and the temperature can be raised even more by the addition of specific polycarboxylates as well as $MgSO_4$ and $Na_5P_3O_{10}$.

TABLE 3

Decomposition Temperature of Peracid Granular Materials

| Example | 4 | 5 | 6 | 7 | 8 | 9 | 10 | 11 |
|---|---|---|---|---|---|---|---|---|
| temperature (°C.) | 92 | 95 | 123 | 107 | 135 | 125 | 130 | 129 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for preparing a stabilized bleaching agent containing a water-insoluble diperoxydicarboxylic acid, comprising the steps of:
   a) peroxygenating a water-insoluble dicarboxylic acid in the presence of hydrogen peroxide and sulfuric acid, and then separating the resulting product into a diperoxydicarboxylic acid-containing suspension, said suspension containing less than 10% sulfuric acid based on the liquid phase of said suspension, and a substantially peroxide-free filtrate containing a majority of the sulfuric acid, in a multi-stage filtration cascade;
   b) neutralizing said filtrate to a pH of 2-6 by adding a sodium hydroxide solution, said solution containing up to 30 ppm heavy metals and up to 50 ppm chloride ions, cooling said neutralized filtrate to crystallize Glauber's salt, recovering said Glauber's salt, and then heating said recovered Glauber's salt to form sodium sulfate;
   c) adjusting said suspension to a pH of 2-6 by adding a sodium hydroxide solution, said solution containing up to 30 ppm heavy metals and up to 50 ppm chloride ions, at a temperature below about 40° C.;
   d) adding 2-200 wt.%, based on the diperoxydicarboxylic acid content, of a water soluble organic polymer to said adjusted suspension, to obtain a suspension/polymer mixture; and
   e) agglomerating said suspension/polymer mixture with said sodium sulfate and drying said agglomerates to produce said stabilized bleaching agent.

2. The process of claim 1, wherein said sodium hydroxide solution in steps b) and c) comprises up to 50 wt.% sodium hydroxide.

3. The process of claim 1, wherein said sodium sulfate has a bulk density of 1000-1500 g/l and a particle size distribution in which at least 90% of the particles have a particle size below 200 microns.

4. The process of claim 1, wherein said sodium sulfate contains up to 30 ppm heavy metals, up to 50 ppm chloride ions and less than 5 wt.% water.

5. The process of claim 1, wherein said diperoxydicarboxylic acid-containing suspension contains up to 30 ppm heavy metals and up to 50 ppm chloride ions.

6. The process of claim 1, wherein said stabilized bleaching agent has a particle size distribution in which at least 90% of the particles have a particle size in the range of 200-1250 microns and said bleaching agent has a bulk density in the range from 400-800 g/l.

7. The process of claim 1, wherein said stabilized bleaching agent produces less than 6 wt.% dust when the abrasion resistance of said bleaching agent is measured by tumbling for 2 hours on an Engelsmann tumble filter with a screen aperture of 200 microns.

8. The process of claim 1, wherein said diperoxydicarboxylic acid comprises an alpha, omega-diperoxydicarboxylic acid having 9-13 carbon atoms or mixtures thereof.

9. The process of claim 8, wherein said diperoxydicarboxylic acid comprises diperoxydodecanedioic acid, diperoxybrassylic acid or mixtures thereof.

10. The process of claim 1, wherein said peroxygenating step comprises contacting a solid water insoluble dicarboxylic acid with a mixture comprising 50-70 wt.% sulfuric acid, 4-20 wt.% hydrogen peroxide and 20-46 wt.% water at a temperature from about 30°-50° C. for from 4-14 hours.

11. The process of claim 10, wherein said resulting product contains up to 40 ppm heavy metals and up to 20 ppm chloride ions.

12. The process of claim 1, wherein said peroxygenating step is conducted in a continuous three-step agitated vessel cascade.

13. The process of claim 1, wherein said peroxygenating step is conducted while avoiding zones of almost dry diperoxydicarboxylic acid.

14. The process of claim 1, wherein said resulting product comprises from 1-25 wt.% diperoxydicarboxylic acid and 50-70 wt.% sulfuric acid, and said resulting product is diluted with 0.1-5.5 parts of water per part of said resulting product, said diluted resulting product is separated in a multi-stage filtration cascade, in which the filtrate from a single stage filtration is recycled into the preceding filtration stage to produce a diperoxydicarboxylic acid-containing suspension containing less than 10% sulfuric acid based on the liquid portion of said suspension and a substantially peroxide-free filtrate containing 10-40 wt.% diperoxydicarboxylic acid and 10-40 wt.% sulfuric acid based on the total weight of the suspension.

15. The process of claim 14, wherein said resulting suspension is diluted with 0.5-2.5 parts water.

16. The process of claim 1, wherein said resulting suspension is separated in a two-four step continuous filtration cascade.

17. The process of claim 16, wherein said resulting suspension is separated in a three-step continuous filtration cascade.

18. The process of claim 14, wherein said diperoxydicarboxylic acid suspension comprises less than 5 wt.% sulfuric acid.

19. The process of claim 14, wherein said diperoxydicarboxylic acid suspension comprises 20-35 wt.% diperoxydicarboxylic acid.

20. The process of claim 14, wherein said substantially peroxide-free filtrate comprises 25-35 wt.% sulfuric acid.

21. The process of claim 1, wherein said filtration is conducted with agitated filter cartridges while agitating said suspension.

22. The process of claim 21, wherein said agitated filter cartridges are arranged radially.

23. The process of claim 1, wherein said filtration is conducted using cross flow microfiltration.

24. The process of claim 1, wherein said sodium sulfate has a particle size distribution wherein at least 90% of said particles have a particle size below 100 microns.

25. The process of claim 1, wherein said adjusting step is conducted at a temperature below 20° C.

26. The process of claim 1, wherein the sodium hydroxide solution used in said adjusting step is at least partially replaced by magnesium oxide or magnesium hydroxide.

27. The process of claim 1, wherein 5-50 wt.% of said organic polymer is added.

28. The process of claim 1, wherein said organic polymer is a polycarboxylic acid.

29. The process of claim 1, wherein said organic polymer is a homopolymer of unsaturated carboxylic acids, a copolymer of unsaturated carboxylic acids or a mixture thereof.

30. The process of claim 29, wherein said unsaturated carboxylic acids are selected from the group consisting of acrylic acid, maleic acid and crotonic acid.

31. The process of claim 29, wherein said copolymers of unsaturated carboxylic acids comprise ethylene, propylene, butene, vinylacetate or styrene comonomers.

32. The process of claim 1, further comprising adding stabilizing additives to said adjusted suspension prior to adding said organic polymer, wherein said additives contain up to 30 ppm heavy metals and up to 50 ppm chloride ions.

33. The process of claim 32, wherein said additives are located in the spacial vicinity of said diperoxydicarboxylic acid in said stabilized bleaching agent.

34. The process of claim 1, wherein said stabilized bleaching agent comprises 5-43 wt.% diperoxydicarboxylic acid.

35. The process of claim 34, wherein said stabilized bleaching agent comprises 12-30 wt.% diperoxydicarboxylic acid.

36. The process of claim 1, wherein said mixing and drying steps are carried out in a continuous multi-step fluid bed granulator, wherein said suspension/polymer mixture is contacted with a sodium sulfate fluid bed at temperatures ranging from 25°-60° C. for a period of time ranging from 20-60 minutes.

37. The process of claim 36, wherein said mixing and drying steps are conducted in a two-five step fluid bed granulator.

38. The process of claim 36, wherein said fluid bed temperature ranges from 30°-40° C.

39. The process of claim 1, wherein said mixing and drying steps are conducted using a spray mix process by agitating said sodium sulfate and spraying said sodium sulfate with said adjusted suspension.

40. The process of claim 1, wherein said drying step comprises drying said mixture continuously in a multi-step fluid bed dryer for a period of time ranging from 10-60 minutes to produce said bleaching agent, wherein the temperature in said fluid bed does not exceed 60° C. and wherein said stabilized bleaching agent contains less than 10 wt.% residual moisture.

41. The process of claim 40, wherein said stabilized bleaching agent contains less than 5 wt.% residual moisture.

* * * * *